United States Patent
Halbheer et al.

(10) Patent No.: US 10,746,311 B2
(45) Date of Patent: Aug. 18, 2020

(54) VALVE DEVICE FOR SWITCHGEARS OR SIMILAR, AS WELL AS USES THEREOF

(71) Applicant: Trafag AG, Bubikon (CH)

(72) Inventors: Remo Halbheer, Hinwil (CH); Dieter Zeisel, Forch (CH)

(73) Assignee: Trafag AG, Bubikon (CH)

( * ) Notice: Subject to any disclaimer, the term of this patent is extended or adjusted under 35 U.S.C. 154(b) by 10 days.

(21) Appl. No.: 16/319,801

(22) PCT Filed: Jun. 22, 2017

(86) PCT No.: PCT/EP2017/065470
§ 371 (c)(1),
(2) Date: Jan. 22, 2019

(87) PCT Pub. No.: WO2018/015101
PCT Pub. Date: Jan. 25, 2018

(65) Prior Publication Data
US 2019/0234521 A1    Aug. 1, 2019

(30) Foreign Application Priority Data

Jul. 20, 2016  (DE) .................. 10 2016 113 339
Dec. 6, 2016   (DE) .................. 10 2016 123 588

(51) Int. Cl.
*F16K 11/22*    (2006.01)
*F16K 27/02*    (2006.01)
(Continued)

(52) U.S. Cl.
CPC ............ *F16K 11/22* (2013.01); *F16K 11/044* (2013.01); *F16K 27/0263* (2013.01);
(Continued)

(58) Field of Classification Search
None
See application file for complete search history.

(56) References Cited

U.S. PATENT DOCUMENTS 3,390,241 A * 6/1968 Frowein ............... H01H 33/563
                                                218/43
4,150,495 A * 4/1979 Stern .................... B41F 23/0426
                                                101/424.1
(Continued)

FOREIGN PATENT DOCUMENTS

CN       201327795 Y    10/2009
CN       204230155 U     3/2015
GB          347172 A *   4/1931 ............. G01L 17/00

*Primary Examiner* — John Fox
(74) *Attorney, Agent, or Firm* — Nelson Mullins Riley & Scarborough LLP; Kongsik Kim, Esq.

(57) ABSTRACT

To improve the reliability of gas space monitoring of a gas space (17) of an electrical system (40) filled with a harmful gas, the invention provides a multi-path valve device (44) for connecting a density monitor (20) to a system to be monitored for gas density, comprising a first gas connection (13) for connecting the valve device (44) to the system, a second gas connection (14) for connection to the density monitor (20), a third gas connection (15) for connection of a testing device (19) for testing the function of the density monitor (20), and switching device for selectively connecting the second gas connection (14) to the first gas connection (13) or the third gas connection (15).

13 Claims, 6 Drawing Sheets

(51) Int. Cl.
*G01N 9/26* (2006.01)
*F16K 11/044* (2006.01)
*G01N 1/20* (2006.01)
*G01N 33/00* (2006.01)

(52) U.S. Cl.
CPC ............. *G01N 1/2035* (2013.01); *G01N 9/26* (2013.01); *G01N 33/0006* (2013.01); *G01N 33/007* (2013.01); *G01N 2001/205* (2013.01)

(56) References Cited

U.S. PATENT DOCUMENTS

| | | | | |
|---|---|---|---|---|
| 4,278,636 | A * | 7/1981 | Voigt | G01N 33/0006 422/84 |
| 5,313,839 | A * | 5/1994 | Ridenour | G01L 19/003 73/706 |
| 5,388,451 | A * | 2/1995 | Stendin | H02B 13/065 218/43 |
| 5,502,290 | A * | 3/1996 | Koyanagi | H01H 33/34 218/78 |
| 2005/0072479 | A1* | 4/2005 | Wuollet | F16K 11/044 137/625.48 |
| 2015/0308938 | A1* | 10/2015 | Scheucher | G01N 33/0006 73/1.06 |

* cited by examiner

VALVE DEVICE FOR SWITCHGEARS OR SIMILAR, AS WELL AS USES THEREOF

CROSS-REFERENCES TO RELATED APPLICATIONS

This application is a U.S. national phase application, pursuant to 35 U.S.C. § 371, of PCT/EP2017/065470, filed Jun. 22, 2017, designating the United States, which claims priority to German Application No. 10 2016 113 339.6, filed Jul. 20, 2016 and German Application No. 10 2016 123 588.1, filed Dec. 6, 2016. The entire contents of the aforementioned patent applications are incorporated herein by this reference.

The invention relates to a valve device for connecting a density monitor or the like to a system to be monitored for gas density or the like. The invention also relates to a monitoring system provided with such a valve device and to a monitoring arrangement provided with such a monitoring system. Finally the invention relates to an electrical system provided with such a valve device, monitoring system or monitoring arrangement.

DE 10 2010 055 249 A1 discloses a density monitor for monitoring a gas density in a measuring volume with a membrane which is connected to the measuring volume in such a way that it moves in the measuring volume when a gas density changes, and a membrane movement detection device connected to the membrane for converting the membrane movement into an electrical signal.

For the technological background to density monitors reference is made in particular to JPS5578231A, U.S. Pat. Nos. 1,527,597 A, 3,431,785 A, 6,125,692 A, 2,662,394 A, 5,421,190 A and DE 10232823 A.

Density monitors are measuring devices for monitoring a gas density of a gas to be monitored. As known from DE 10 2010 055 249 A1, density monitors are used in particular to monitor the density of gases, such as SF6, present as insulators in gas-insulated high- and medium-voltage installations, such as high-voltage switching systems, converters, pipelines, switching devices and transformers.

For this purpose, density monitors based on electronic measuring principles are known, for example, from DE 10232823 A1, which are provided with an electronic density sensor as a measured value transmitter, which has an oscillating quartz crystal arranged in the gas and supplies a frequency signal proportional to the density of the gas as a measured value, the frequency signal being fed to an electronic evaluation unit.

On the market, on the other hand, density monitors based on mechanical measuring principles have established themselves. Due to their mechanical measuring principle, they operate very reliably and with low maintenance even over very long periods of time. In the simplest and most frequently encountered case, a diaphragm working via a reference volume is in contact with the measuring volume, whereby a diaphragm movement caused by a change in the gas density actuates a switch. In the case of the density monitor known from DE 10 201 0 055 249 A1, for example, a diaphragm of a metal bellows is connected to a switch so that a diaphragm movement exceeding a minimum distance triggers a switching operation.

A density monitor having a switching device with a mercury switch is known from DE 27 51 206 A1.

A device for monitoring the density of a gas is known from DE 27 44 549 A1, which comprises a manometer with a pointer and a tube spring as expansion element and a compensation element between the pointer and the expansion element. A segment lever is provided to drive the pointer.

A density monitor for monitoring the density of a gas in a hermetically sealed container is known from the DD 282 076 A5, which enables the longest possible maintenance-free operating time even with smaller leaks in the container. Two metal bellows are provided for this purpose. A push rod is provided between the metal bellows, which actuates a switch in the form of a double switch via a driver and a switching lever. When a first switching contact is closed, a pre-warning signal is emitted. When there is a further loss of density, a second switching contact is closed, with which a solenoid valve is actuated to refill gas into the container until the contacts are opened again.

The density monitors are used in particular to monitor gas spaces filled with gases of concern for the environment, in particular for leaks. The density monitors should therefore operate very reliably and also provide reliable warning signals—even over long periods of time—in the event of critical changes in gas density.

The object of the invention is to provide a simple way to further improve the reliability of monitoring a gas space filled with a harmful gas.

This object is achieved by a device according to claim 1. Advantageous embodiments are the subject of the sub-claims. Combinations of the device with a monitoring device, e.g. a density monitor or a system to be monitored, are described in the independent claims.

According to a first aspect, the invention relates to a multi-path valve device for connection of a monitoring device for monitoring at least one gas parameter to an electrical system containing a harmful gas and to be monitored for the gas parameter, the valve device comprising a first valve path designed as a gas connection for connecting the valve device to the system, a second valve path designed for a gas transfer to the monitoring device, a third valve path designed for a gas transfer to a testing device for testing at least one function of the monitoring device, and an automatic switching device for selectively automatically connecting the second valve path to the first valve path or to the third valve path.

The monitoring device preferably comprises a density monitor and/or a pressure sensor. In a preferred embodiment, a density monitor is provided, which selectively or in combination detects both the gas density and the pressure of the gas to be monitored.

It is preferred that the second valve path includes a check valve arrangement, which is pre-loaded into a closing position for closing the second valve path and which can be moved to the opening position by connecting the monitoring device.

It is preferred that the check valve arrangement has a check valve opener pre-loaded into its closing position which, when the monitoring device is connected, is engaged by a connecting element of the monitoring device in order to move the opener against its pre-load to its opening position by connecting the monitoring device.

It is preferred that the switching device includes a valve tappet which is pre-loaded into a first switching position in which the third gas connection is closed and the first gas connection is connected to the second valve path and which can be moved into a second switching position in which the first gas connection is closed and the second valve path is connected to the third gas connection by connecting the testing device.

It is preferred that the valve tappet comprises a projection or pin which, when the testing device is connected, is engaged by a connecting element of the testing device and is urged against its pre-load from the first switching position to the second switching position.

It is preferred that at least one sensor device for detecting at least one parameter selected from the group of parameters comprising temperature, density, pressure, humidity, type of gas and presence of a decomposition product is in fluid communication with the first gas connection and/or the second valve path.

It is preferred that the first valve path is designed as a first gas connection.

It is preferred that the second valve port is designed as a second gas connection for connecting the monitoring device to the multi-path valve device.

It is preferred that the third valve path is designed as a third gas connection for connecting the testing device.

According to a further aspect, the invention provides a monitoring device comprising a multi-path valve device according to one of the above-mentioned configurations and a monitoring device for monitoring at least one gas parameter of a harmful gas in an electrical system.

It is preferred that the monitoring device and the multi-path valve device are formed separately, with the monitoring device being connectable to the second valve path.

In a different configuration, it is preferred that the monitoring device and the multi-path valve device are integrated into a common unit or common housing.

It is preferred that the monitoring device at least comprises a density monitor and/or a sensor device.

According to another aspect, the invention provides a monitoring arrangement comprising a monitoring device according to one of the above configurations, and a testing device for testing at least one function of the monitoring device.

It is preferred that the testing device can be or is connected to the third valve path designed as a third gas connection.

According to another aspect, the invention provides an electrical system comprising a gas space filled with a harmful gas and a multi-path valve device according to one of the above configurations for connecting a monitoring device for monitoring at least one gas parameter to the gas space.

Alternatively, the system comprises a monitoring device according to one of the above configurations.

Alternatively, the system comprises a monitoring arrangement according to one of the above configurations.

In one configuration, the invention provides a multi-path valve device for connecting a monitoring device for monitoring at least one gas parameter to a system containing a harmful gas and to be monitored for said gas parameter, comprising a first gas connection for connecting a valve device to the system, a second gas connection for connection to the monitoring device, a third gas connection for the connection of a testing device for testing the function of the monitoring device, and a switching device for automatically selectively connecting the second gas connection to the first or to the third gas connection.

In a preferred configuration, the invention relates to a multi-path valve device for connecting a density monitor to a system to be monitored for gas density, comprising a first gas connection for connecting the valve device to the system, a second gas connection for connection to the density monitor, and a third gas connection for the connection of a testing device for testing the function of the density monitor, and a switching device for automatically selectively connecting the second gas connection to the first or to the third gas connection.

It is preferred that the second gas connection comprises a check valve arrangement which is pre-loaded into a closing position to close the second gas connection and which can be moved to the opening position by connecting the monitoring device, in particular the density monitor.

It is preferred that the switching device includes a valve device, in particular a valve tappet, which is pre-loaded into a first switching position in which the third gas connection is closed and the first gas connection is connected to the second gas connection and can be moved to a second switching position in which the first gas connection is closed and the second gas connection is connected to the third gas connection by connecting the testing device to the third gas connection.

Preferably, the check valve arrangement comprises a check valve opener pre-loaded into its closing position which, when the monitoring device is connected, is engaged by a connecting element of the monitoring device in order to move the opener against its pre-load it to its opening position by said connecting action.

Preferably, the valve device, in particular the valve tappet, comprises a projection or pin which, when the testing device is connected, is engaged by a connecting element of the testing device and is urged against its pre-load from the first switching position to the second switching position.

It is preferred that at least one sensor device for detecting at least one parameter selected from the group of parameters comprising temperature, density, pressure, humidity, type of gas and presence of a decomposition product is in fluid communication with the first gas connection and/or the second gas connection.

According to another aspect, the invention provides a monitoring arrangement, in particular a density monitoring arrangement, comprising a multi-path valve device according to one of the above configurations and a monitoring device, in particular a density monitoring device with a gas parameter sensor, in particular a density monitor, with said monitoring device being connectable to the second gas connection.

A preferred configuration of the monitoring arrangement comprises a testing device to be connected to the third gas connection for testing a switching point and/or a function of the monitoring device, in particular the density monitor.

According to another aspect, the invention provides an electrical system, in particular a switching system, comprising a gas space filled with a gas to be monitored for its density and a multi-path valve device according to one of the preceding configurations to connect a density monitor and/or a monitoring device to the gas space.

In particular, the invention provides a simple way of checking the function of gas monitoring devices from time to time. In particular, in the case of density monitors mounted on electrical systems such as switchgears, it is desirable that the condition or switching points of the density monitor can be checked at any time without dismantling them. The same applies to the density sensors or generally to sensors used for monitoring the condition of the system (e.g. humidity sensors, sensors measuring the chemical decomposition of the insulation gas SF6, e.g. SF4, WF6, SOF4, SO2F2, SOF2, SO2 and/or HF; but also detecting oils and dust).

In accordance with a preferred embodiment of the invention, a modular 3-way valve is proposed for this purpose, which preferably adapts to tank bottles from different manufacturers.

Up to now it was common to use a check valve between the density monitor and the tank, which is now no longer necessary when using the three-path valve. In an advantageous design, it is intended to install other sensors in the flange connection, which should measure as directly as possible in the gas space, so that they provide better measurements. Preferred designs comprise a humidity sensor, a gas quality sensor and/or a temperature sensor. A simple density sensor and a mixed gas density sensor for binary mixtures (pressure/temperature/density) could also benefit from this positioning.

A preferred embodiment of the invention also relates to an automatic 3-way valve for SF6 density monitors.

In accordance with a preferred embodiment, the invention provides a modular 3-way valve for use on an electrical switchgear, the valve (1) allowing a functional check of the sensor/monitor when installed and/or (2) comprising an additional sensor system (e.g. for humidity, concentration, electric arc monitoring, decomposition products or the like), which can preferably also be checked.

A preferred use of the invention or its embodiments concerns the case of a density monitor mounted to an electrical switchgear. An advantage of preferred embodiments is that the condition or the switching points of the monitor can be checked at any time without dismantling. The same applies to density sensors or sensors in general as they are used for monitoring the condition of the system. Examples are humidity sensors, sensors which measure the chemical decomposition of the insulation gas SF6, e.g. SF4, WF6, SOF4, SO2F2, SOF2, SO2 and/or HF, but also oils and dust. Even if the embodiment of the invention is described using the example of a density monitor particularly suitable for SF6, other gases, in particular insulation gases, can also be monitored and the monitoring device checked in other applications.

In one embodiment, an automatic 3-way valve, which is directly integrated into the density monitor, is proposed to allow checking of the density monitor without disassembly.

In one embodiment, it is intended to mount a separate 3-way valve to the switchgear and to attach the density monitor to it. With the automatic 3-way valve, which is directly integrated into the density monitor, this additional part can be omitted.

A particularly preferred embodiment of the monitoring device relates to a density monitor or gas parameter sensor (pressure, temperature, humidity, . . . ) with integrated automatic 3-way valve for use with electrical switchgears, which permits a functional check of the sensor/monitor when installed.

Two exemplary embodiments will be described in more detail below with reference to the attached drawings. In the drawings it is shown by.

In the following, exemplary embodiments of an electrical system 40 with a gas space 17 filled with insulating gas and a monitoring arrangement 42 will be explained in more detail with reference to the attached drawing figures. First, reference is made to FIG. 4, which shows a schematic overview.

Figure 4:
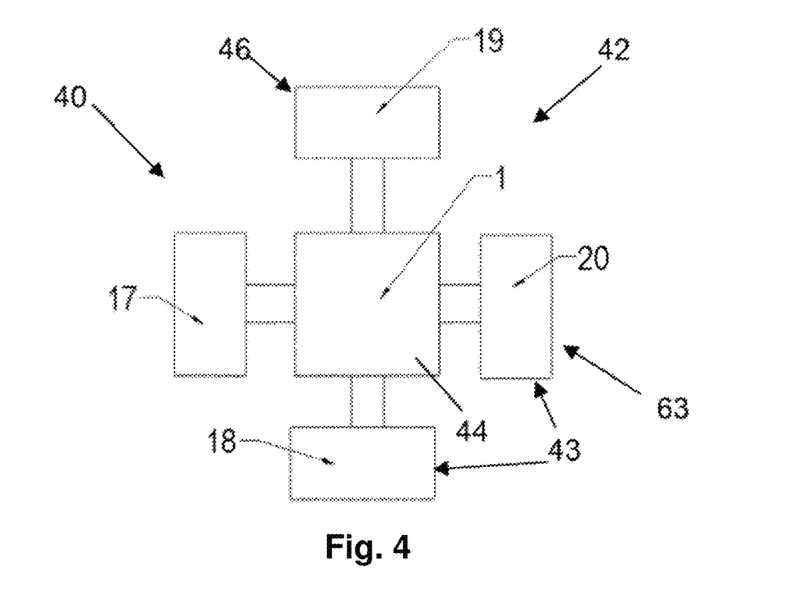
FIG. 4 a schematic representation of the switchgear including the monitoring device.

The electrical system 40 is in particular a gas-insulated medium-voltage system or high-voltage system, such as a switchgear, a voltage transformer, a high- or medium-voltage pipeline, a switching device or a transformer. The lines carrying the high voltage or medium voltage are housed within a closed gas space 17, which contains an insulating gas, such as SF6 in particular, or an insulating gas mixture, e.g. with SF6 and other gas components.

A monitoring arrangement 42 is connected to the gas space 17 for monitoring the gas space 17, in particular for monitoring the gas density and/or other parameters, such as in particular temperature, humidity, gas composition, pressure, etc. The monitoring arrangement 42 has a monitoring system 43 for this purpose. The monitoring system 43 has a monitoring device 63 and a multi-path valve device 44 for connecting the monitoring device 63 to the gas space 17.

Figure 1:
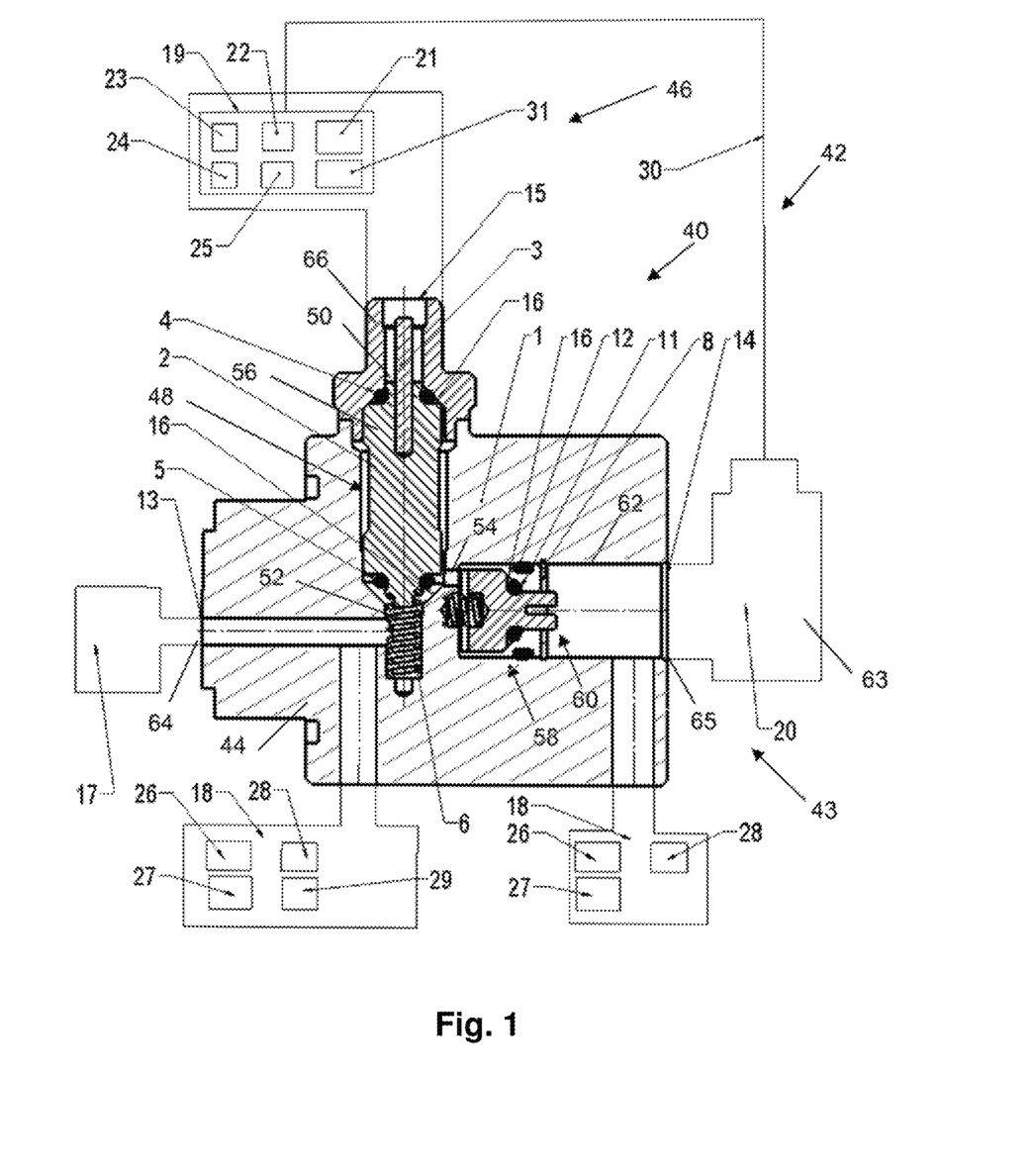
FIG. 1 a partly sectional representation of a first embodiment of a monitoring arrangement for monitoring the gas space of an electrical high-voltage or medium-voltage installation, such as in particular a switchgear, the gas space being filled with an insulating gas or protective gas, the monitoring arrangement having a monitoring system or a monitoring device, in particular a density monitor, for monitoring at least one gas parameter of the insulating gas or protective gas and a multi-path valve device for connecting the monitoring device to the gas space and for optionally connecting the monitoring system to a testing device.
Figure 2:
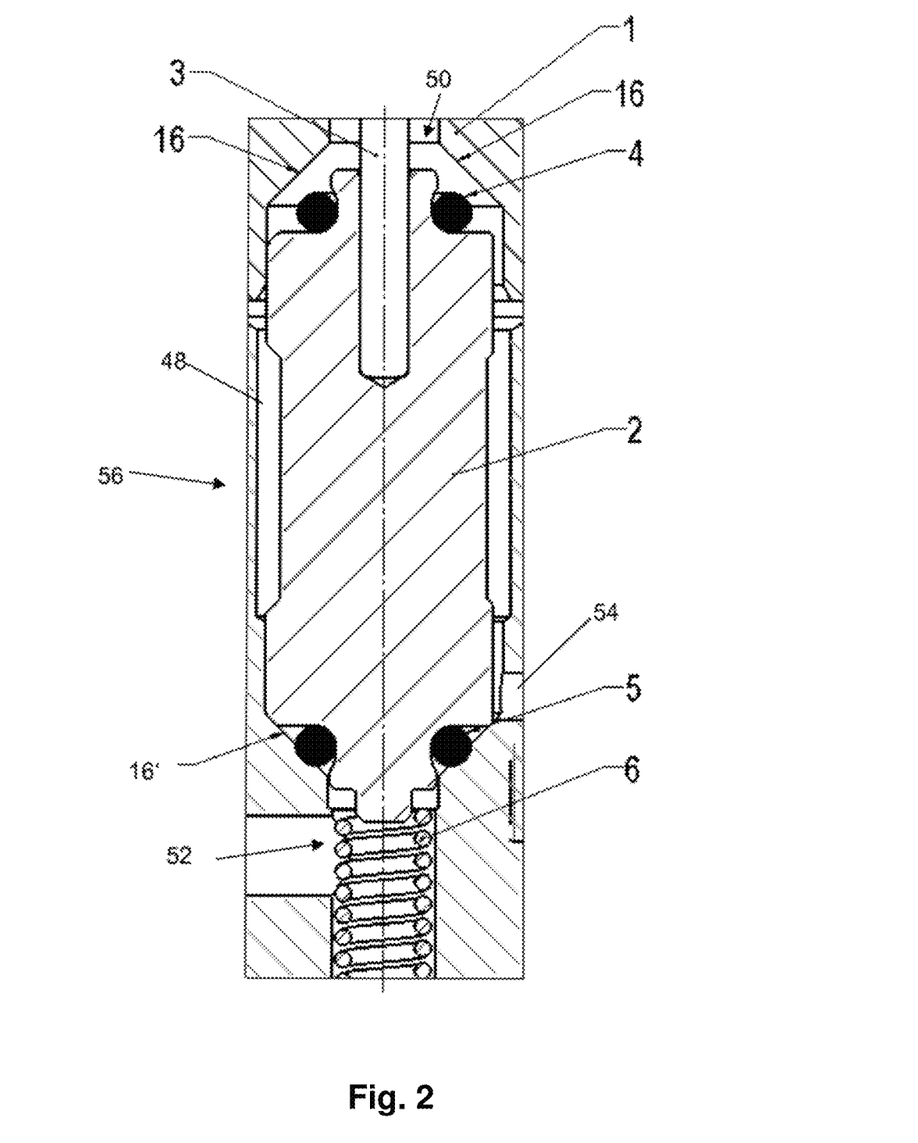
FIG. 2 an enlarged view of a detail of the multi-path valve device in the region of a gas connection for connecting a testing device.
Figure 3:
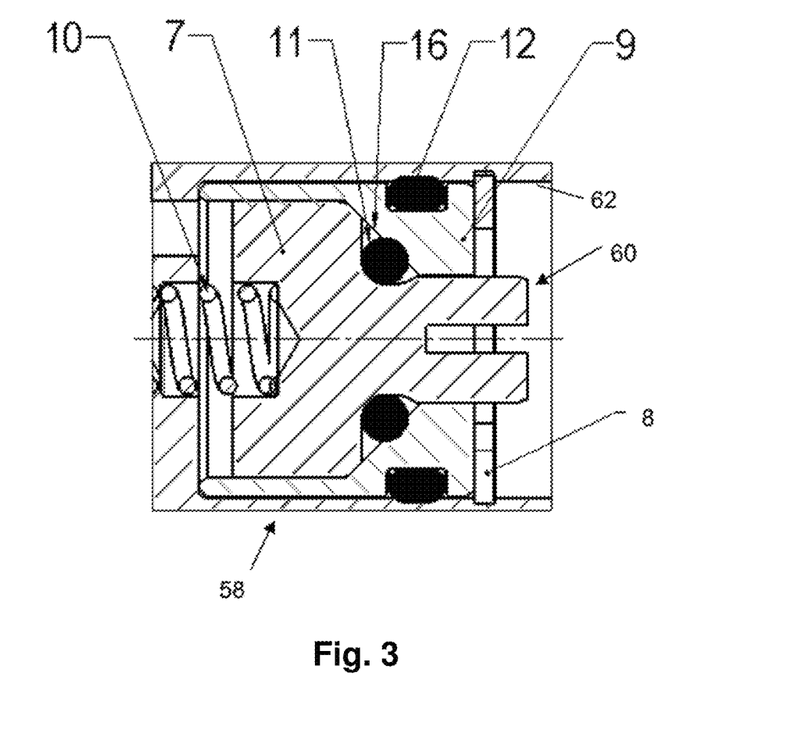
FIG. 3 an enlarged view of a detail of the multi-port valve device in the region of a gas connection for connecting a monitoring device.

In the first embodiment of the monitoring system 43, which is illustrated in the FIGS. 1 to 3, the monitoring device 63 and the multi-path valve device 44 are formed separately. In the second embodiment of the monitoring system 43, the multi-path valve device 44 and the monitoring device 63 are integrated into one unit.

In both embodiments, the multi-path valve device 44 is designed for connecting the monitoring device 63, which is configured to monitor at least one gas parameter, to an electrical system 40 containing a harmful gas and to be monitored for the gas parameter. The multi-path valve device 44 comprises a first valve path 64 for connecting the valve device 44 to the system 40, a second valve path 65 adapted for gas transfer to the monitoring system 43, a third valve path 66 adapted for gas transfer to a testing device 19 for testing at least one function of the monitoring device 63, and an automatic switching device 56 for selectively automatically connecting the second valve path 65 to the first valve path 64 or the third valve path 66. The FIGS. 1 to 4 below are used to explain the first embodiment in more detail.

The multi-path valve device 44 in the first embodiment has a first gas connection 13 for connecting the gas space 17, a second gas connection 14 for connecting the monitoring system 43 and a third gas connection 15 for connecting a testing system 46, by means of which at least one function of the monitoring system 43 can be tested. The first gas connection 13 is formed at the first valve path 64, the second gas connection 14 is formed at the second valve path 65, and the third gas connection 15 is formed at the third valve path 66. The gas connections 13, 14, 15 can, for example, be formed with a thread for connecting respective gas pipes. Other gas connection types are of course also conceivable.

The multi-path valve device 44 is designed for automatically switching and connecting the gas connections 13, 14, 15. The multi-path valve device 44 is preferably designed in such a manner that, when only the gas space 17 is connected to the first gas connection 13 and no device is connected to the other gas connections 14, 15, said other gas connections 14 and 15 are closed.

The multi-path valve device 44 is preferably designed in such a manner that, when the monitoring system 43 is connected to the second gas connection 14, but the third gas connection 15 remains unused, the first gas connection is in fluid communication with the second gas connection so that the gas space 17 is in fluid communication with the monitoring system 43 so that the gas space 17 can be monitored by means of the monitoring system 43.

Preferably, the multi-path valve device 44 is further designed in such a manner that, when the testing system 46 is connected to the third gas connection 15, automatic switching of the fluid communication between the gas connections 13, 14, 15 takes place in such a way that the first gas connection 13 is closed and the second gas connection 14 is in communication with the third gas connection 15 so that the monitoring arrangement 42 connected to the second gas connection 14 can be tested by means of the testing system 46 for at least one function.

For example, the testing system 46 can be constituted by a mobile testing device 19 which may be connected to the respective third gas connection as required to test several such monitoring systems 43 in order to immediately carry out a test of the monitoring system 43 during its ongoing operation, without dismantling or other effort and without impairing the tightness or gas safety of the monitoring system 43.

FIG. 1 shows the overall construction, FIG. 2 shows the design of the multi-path valve device 44 in the region of the third gas connection 15, and FIG. 3 shows the design of the multi-path valve device 44 in the region of the second gas connection 14.

As can be seen from FIG. 1, the multi-path valve device 44 has a valve housing 1 in which the gas connections 13, 14, 15 are installed, e.g. with corresponding connection threads (not shown).

The gas space 17 can be constituted by a tank from different manufacturers. The first gas connection 13 can be connected e.g. with different adapters (not shown) to different tank nozzles.

In the region of the third gas connection 15, a valve tappet 2 is provided as normally closed and normally open. The valve tappet 2 can be moved between a closing position and an opening position by means of a sensor which detects the connection of a testing system 46.

For this purpose, the valve tappet 2 in particular has a cylinder or pin 3 for an automatic closing and opening function in such a way that the cylinder or pin 3 projects towards the end region of the third gas connection 15 and, when the testing system 46 is connected, is pushed into the valve housing 1 in order to move the valve tappet 2 from its closing position into its opening position.

As can be seen in FIG. 2 in particular, the valve tappet 2 is accommodated in a fluid channel space 48 so that it can be moved. At both longitudinal ends of the fluid channel space 48, it has a sealing cone 16, 16'.

At the first end shown in FIG. 2 above, which faces the connection for the testing system 46, a first through-passage 50 to the testing system 46 is provided, which is closed by a first seal 4 when the valve tappet 2 moves against the first sealing cone 16 arranged here.

A second through-passage 52 to the first gas connection 13 is provided at the second end shown in FIG. 2 below, which can be closed by means of a second seal 5 when the valve tappet 2 moves against the second sealing cone 16'. A gap is left between the valve tappet 2 and the wall of the fluid channel space 48. A passage 54 leads laterally into the fluid channel space 48 thus left free and towards the second gas connection 14, which is shown in more detail in FIG. 3.

The valve tappet 2 is preloaded by a compression spring 6 into its closing position shown in FIG. 1. FIG. 2 shows the opening position of valve tappet 2 when the testing system 46 is connected.

In the closing position of the valve tappet 2, the first gas connection 13 is connected to the second gas connection 14 via the second through-passage 52 at the second end of the fluid channel space 48, the fluid channel space 48 and the lateral passage 54. The valve tappet 2 also performs a check valve function by being forced into its closing position by overpressure at the first gas connection 13.

In the opening position of the valve tappet 2, the second through-passage 52 is closed by the second seal 5 applying against the second sealing cone 16' and the first passage 54 is open so that the third gas connection 15 is connected to the second gas connection 14 via the first gas passage 54, the fluid channel space 48 and the passage 54.

The valve tappet 2 thus forms a switching device 56 with which, when the testing system 46 is connected, automatic switching between a first switching position—the closing position—and a second switching position—the opening position—takes place to uncouple the monitoring device from the gas space 17 and couple it to a testing device 19 for testing during operation.

The second gas connection 14 is provided with a check valve assembly 58 shown in more detail in FIG. 3. The check valve assembly 58 has a closing position in which the second gas connection 14 is closed, and an opening position in which the second gas connection 14 is opened, and comprises an opening mechanism 60, which detects a connection of the monitoring system 43 to the second gas connection 14 and automatically moves the check valve arrangement 58 from the closing position into the opening position in response to the connection.

The check valve arrangement 58 is designed in such a manner that it is urged into its closing position in case of an overpressure inside the valve housing 1 and in particular in case of an overpressure on the side of the gas connection 13. Preferably, the check valve arrangement 58 is also preloaded into its closing position, e.g. by means of a compression spring 10.

As can be seen in FIG. 3, in a preferred configuration, the check valve arrangement 58 comprises an opener 7 disposed in a channel opening 62 so that it can be moved for opening and closing the check valve at the connection for the monitoring arrangement 42. Furthermore, a circlip 8 is inserted in the channel opening 62 to secure the check valve arrangement at the connection for the monitoring arrangement 42. The check valve arrangement 58 also has a sleeve 9 with a sealing cone 16 where a seal 11 attached to the opener 7 can seal. The sleeve 9 is sealed externally against the wall of the channel opening 62 by means of a seal 12. The opener 7 is preloaded into its closing position against the sealing cone 16 of the sleeve 9 by means of the compression spring 10.

As shown in FIG. 1, in a preferred configuration, the multi-path valve device 44 comprises a sensor installation 18. In FIG. 1, two possible connections for the sensor installation 18 are indicated. In a first version, the sensor installation 18 is connected to the first gas connection 13 and is thus permanently and/or directly connected to the gas space 17. In a second version, the sensor installation 18 is connected to the second gas connection 14. The first version has the advantage of a direct connection so that temperature, humidity, gas composition can be directly measured. The detection of an electric arc is also possible. The second version has the advantage that the sensor installation 18 can be checked for example by the testing system 46 without dismantling. Accordingly, the sensor installation 18 can be an exemplary embodiment of the monitoring system 43 or can be part of the monitoring system 43.

In a preferred design, the sensor installation 18 includes at least one, several or all of the following sensors: a humidity sensor 26, a temperature sensor 27, a decomposition product sensor 28, an electric arc counter 29 or an electric arc detector, and a pressure sensor.

As indicated in FIG. 1, in a preferred design, the monitoring system 43 includes at least one density monitor 20. In particular, the density monitor 20 is constructed as shown and described in WO 201 5/1 01 442 A1 and DE 10 2013 115 009 A1 to which explicit reference is made for further details.

In a preferred design, the testing system 46 comprises at least one testing device 19 for testing a switching point of the density monitor 20 and/or for testing a function of the density monitor 20 and/or a sensor 26, 27, 28.

In a preferred design, the testing device 19 includes a reference sensor and/or a reference density monitor 21. This allows a signal 30 from the monitoring system 43 delivered e.g. via a line to be compared to a reference value in order to check the function.

In a preferred design, the testing device 19 comprises at least one, several or all of the following units: a pump 20, an indicating device 23, e.g. a display, an electronic control 24, a user interface 25, in particular in the form of a GUI, and/or a memory and/or a microcontroller 31.

The function of the monitoring arrangement 42 herein described will be explained in more detail in the following. In particular, the Figures show a valve with at least three connections 13, 14, 15.

The first gas connection 13 is fixedly connected to the gas space 17, in particular to the one of a switchgear. In this condition, the second gas connection 14 and the third gas connection 15 are closed.

The opener 7 of the check valve is opened and the gas feedthrough from the gas space 17 to the density monitor 20 enabled by connecting the density monitor 20 to the second gas connection 14.

During operation, it is possible to connect a testing device 19 via the third gas connection 15, which is provided for a testing system 46. The gas space 17 of the switchgear or the like is automatically uncoupled from the density monitor 20 and the testing device 19 by means of the valve tappet 2 when the testing device 19 is connected. In the decoupled state of the switchgear, feedthrough is only guaranteed between the density monitor 20—second gas connection 14—and the testing device 19—third gas connection. The testing device 19 uses the enclosed residual gas from the gas space 17 of the switchgear to test the density monitor 20. After testing the density monitor 20, the residual gas is pumped back by the testing device 19. The multi-port valve device 44 automatically switches over again by means of the valve tappet 2 when the testing device 19 is uncoupled.

The second embodiment of the monitoring system 43 will be explained in more detail in the following with reference to the FIGS. 5 to 10.

While in the case of a conceivable use of the first embodiment, a separate 3-way valve is to be mounted to a switchgear and a monitoring device 63, in particular a density monitor 20, is to be attached to this 3-way valve, a preferred use of the second embodiment of the invention provides that an automatic 3-way valve together with the monitoring device 63 is directly integrated into one unit. For example, a multi-path valve device 44 is directly integrated into a density monitor 20.

In the following description of the second embodiment, the same reference signs are used for corresponding parts in the first embodiment, and for further details and functions of these parts, reference is made to the above description of the first embodiment.

Figure 5:
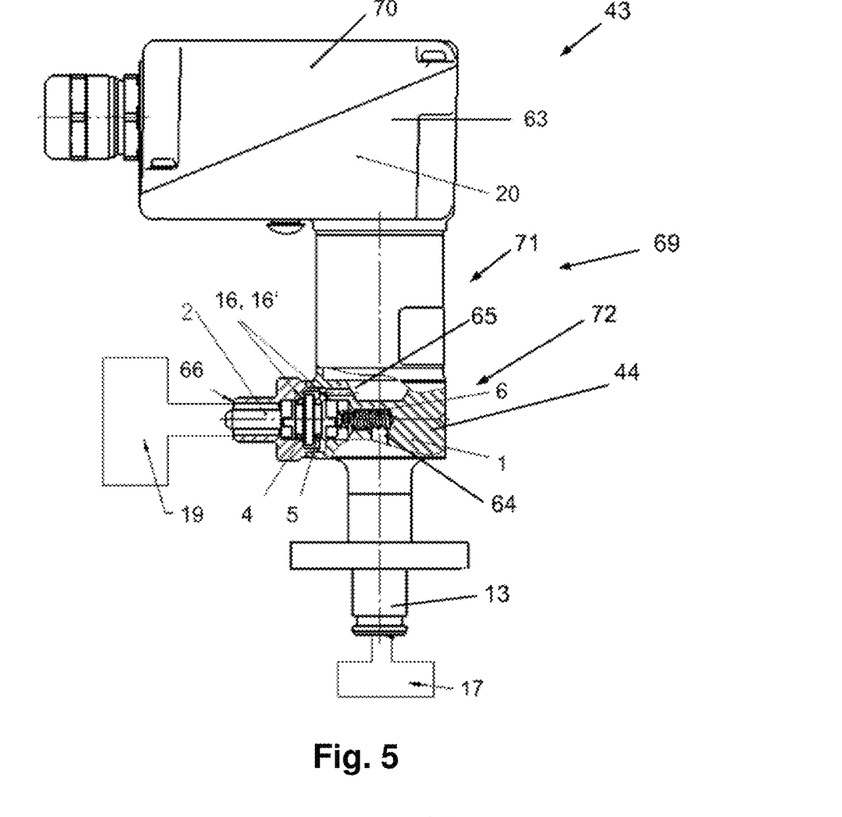
FIG. 5 a representation of a second embodiment of a monitoring device for monitoring the gas space of an electrical high-voltage or medium-voltage installation having an integrated multi-path valve device.
Figure 7:
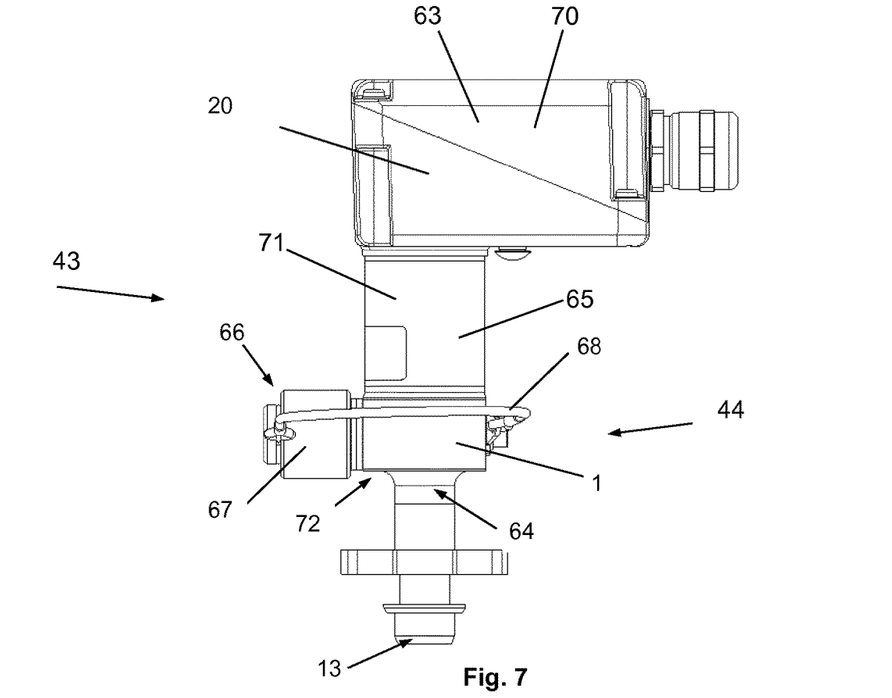
FIG. 7 a first lateral view of the monitoring device of FIG. 5.
Figure 8:
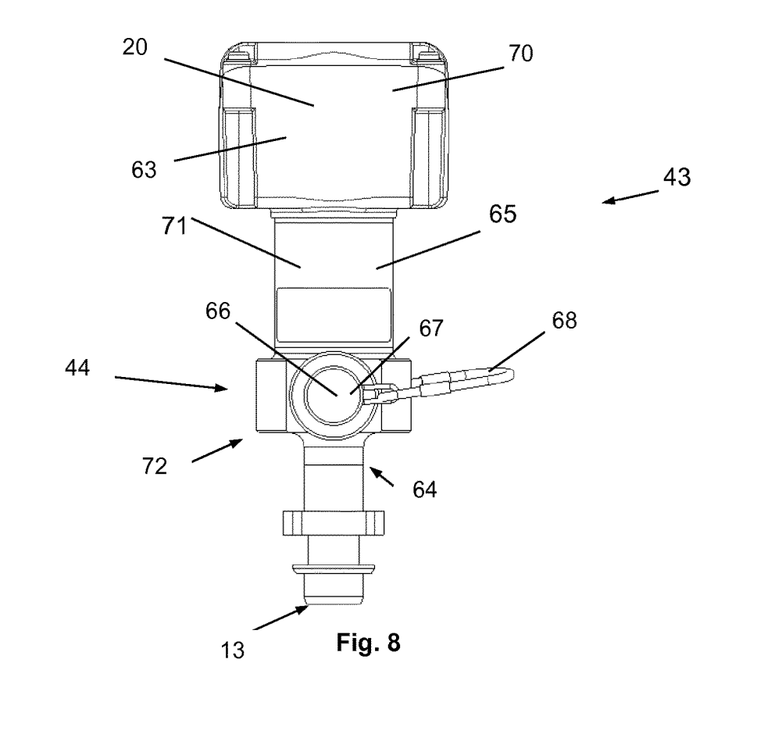
FIG. 8 a front view of the monitoring device of FIG. 5.
Figure 9:
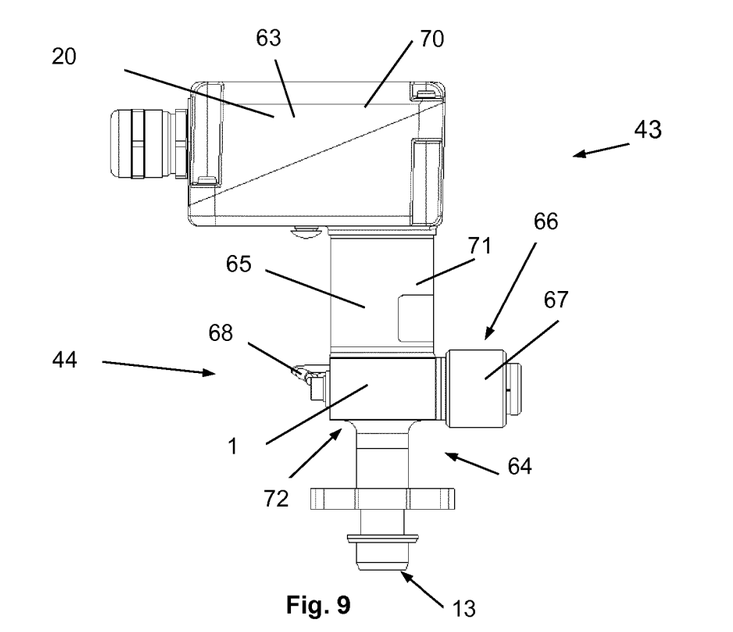
FIG. 9 a further lateral view of the monitoring device of FIG. 5.
Figure 10:
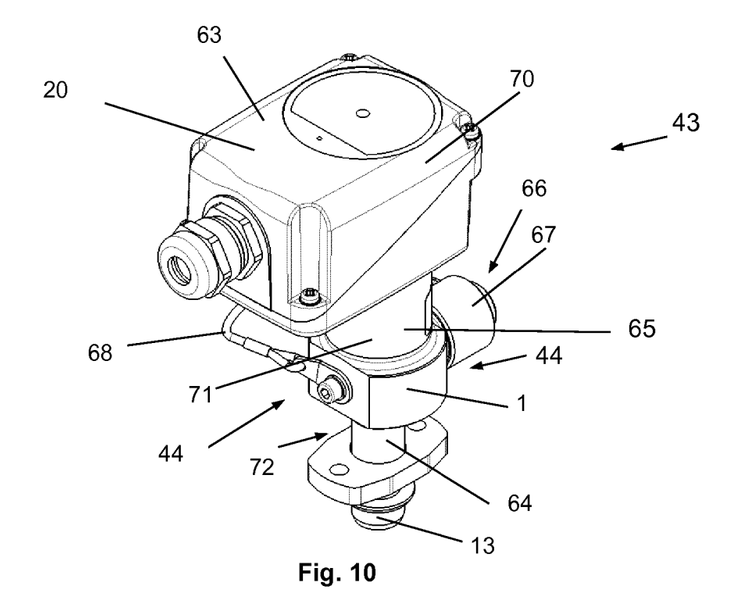
FIG. 10 a perspective view of the monitoring device of FIG. 5.

As can be seen from the FIGS. 5, 7 and 10, the second embodiment of the monitoring system 43 comprises an overall housing 69 composed of several parts which houses the monitoring device 63 and the multi-path valve device 44.

In the illustrated example, the monitoring device 63 has the density monitor 20 in a density monitor housing part 70. The monitoring device 63 is connected to the gas space 17 to be monitored via a tubular connection housing part 71. This connection housing part 71, for example, accommodates a multi-path valve device 44 including an automatic 3-way valve for example.

The first valve path 64 has a first gas connection 13 for connecting the gas space 17. The second valve path 65 is accommodated in the overall housing 69 and servers to transfer the gas to the monitoring device 63 integrated into the overall housing 69. The second valve path is designed, for example, as a gas transfer from the connection housing part 71 to the density monitor housing part 70. The third valve path 66 includes in a preferred design the third gas connection 15 for connecting the testing device 19. In the illustrated design, a protective cap 67, e.g. designed as a threaded cap, can be provided. The protective cap 67 can be secured to one of the housing parts 70, 71 of the overall housing 69 by means of a protective cap securing device 68.

Figure 6:
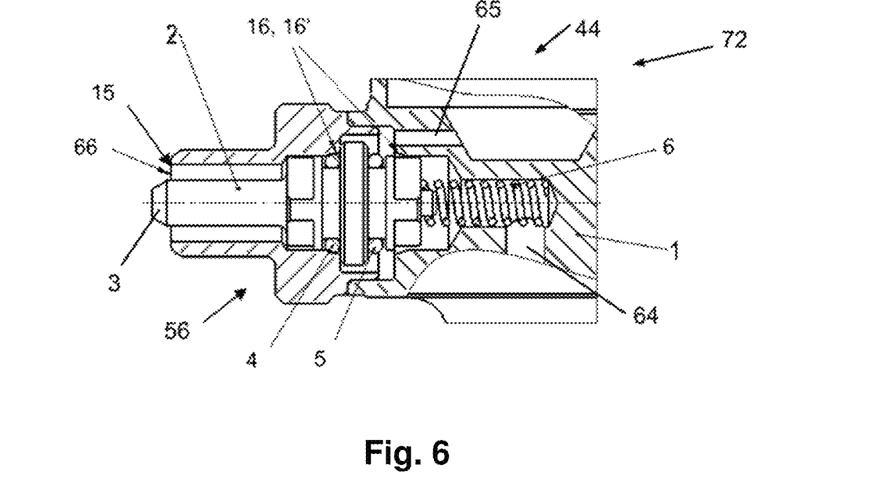
FIG. 6 an enlarged view of a detail of the multi-path valve device in the region of a valve path for connecting a testing device.

A sectional view of the multi-path valve device 44 is shown in the FIGS. 5 and 6. The connection housing part 71 serves as a valve housing, i.e. it has a valve housing region 72 in which the movable valve tappet 2 is housed. As in the first embodiment, the pin 3 intended for the automatic closing and opening function, the seal 4 for the valve intended for the testing connection and the seal 5 for the valve intended for the gas space 17 or for a switchgear, and the compression spring 6 for the valve intended for the test connection are provided.

FIG. 6 shows the valve tappet 2 in its normal position, without the testing device 19 being connected to the third gas connection (test connection or maintenance connection) 15. The compression spring 6 urges the valve tappet 2 to the left in FIG. 6 so that the seal 4 closes the third valve path 66, which in this case leads to the third gas connection 15. The first and the second valve paths 64, 65 are thus in fluid communication whereby the monitoring device 63, in particular the density monitor 20, and the first gas connection 13 are in fluid communication. In this manner, the density monitor can, for example, monitor the gas space 17 connected to the first gas connection 13.

When the testing device 19 is connected, the valve tappet 2 is moved via the pin 3 to the right in FIG. 6, whereby the second valve path 65 is opened and the first valve path 64 is closed by means of the seal 5. In this manner, the monitoring device 63 is in fluid communication with the testing device 19, and the connection to the monitoring gas space 17 is cut off.

The FIGS. 5 to 10 show in particular a density monitor 20 having an integrated maintenance connection (third gas connection). The first gas connection 13 is fixedly connected to the gas space 17 of the switchgear.

In the illustrated normal operation, the third gas connection 15 is closed and the flow from the gas space 17 to the density monitor 20 is guaranteed.

During operation, a testing device 19 can be connected via the third gas connection (gas connection to the test system).

By connecting a testing device 19 to the third gas connection 15, the valve tappet 2 is pushed in and opens the passage from the testing device 19 to the density monitor 20 by this movement. At the same time, the passage from the gas space 17 to the density monitor 20 is closed. The testing device 19 uses the enclosed residual gas of the switchgear to test the density monitor 20. After testing the density monitor 20, the residual gas is pumped back by the testing device 19. When the testing unit (e.g. the testing device 19) is uncoupled, the valve tappet 2 automatically switches over again.

The design shown in the FIGS. 5 to 10 therefore shows a multi-path valve device 44, which is directly integrated into the density monitor 20, which allows the density monitor 20 to be checked without disassembly.

As indicated in FIG. 5, a monitoring system 43 comprises a monitoring device 63 and a multi-path valve device 44. The monitoring device 63 has at least one density monitor 20 with at least one integrated third valve path 66. The first valve path 64 is fixedly connected to the gas space 17 of the switchgear. In this state, the third valve path 66 is closed and the flow from the gas space 17 to the density monitor 20 is guaranteed. Due to the design, it is possible to connect a testing device 19 via the third valve path 66 during operation.

FIG. 6 shows a detail from FIG. 5 and represents a detail of the multi-path valve device 44. By connecting the testing device 19 to the third valve path 66, the valve tappet 2 is pushed in against the spring force of the compression spring 6 and thus opens the passage from the testing device 19 to the density monitor 20, whereby the valve tappet 2 with the seal 5 moves against the sealing cone 16'. When the testing unit is uncoupled, the valve tappet 2 automatically switches over again by moving against the first sealing cone 16.

FIGS. 7 to 10 are further representations of the monitoring system 43. In these embodiments, the third valve path 66 is equipped with the protective cap 67 having the protective cap securing device 68 to prevent contamination of the third valve path 66.

LIST OF REFERENCE NUMBERS

1 valve housing
2 valve tappet: normally open/normally closed
3 cylinder or pin for automatic closing/opening function
4 seal of valve of testing connection
5 seal of valve of switchgear
6 compression spring for valve of testing connection/switchgear
7 opener of check valve of density monitor connection
8 circlip of check valve assembly density monitor connection
9 sleeve of check valve of density monitor connection
10 compression spring for check valve of density monitor connection
11 seal for check valve of density monitor connection
12 seal of check valve assembly
13 first gas connection (in particular switchgear)
14 second gas connection (monitoring device, in particular density monitor)
15 third gas connection (testing system)
16 first sealing cone
16' second sealing cone
17 gas space of switchgear to be monitored
18 sensor installation
19 testing device for switch point or function testing
20 density monitor
21 reference sensor or reference density monitor
22 pump
23 indicating device (display)
24 electronic control
25 GUI=user interface
26 humidity sensor
27 temperature sensor
28 decomposition product sensor
29 electrical arc counter, electrical arc detection
30 signal of installed density monitor to testing device
31 memory & microcontroller
40 electrical system
42 monitoring arrangement
43 monitoring system
44 multi-path valve device
46 testing system
48 fluid channel space
50 first through-passage
52 second through-passage
54 passage
56 switching device
58 check valve arrangement
60 opening mechanism
62 channel opening
63 monitoring device
64 first valve path
65 second valve path
66 third valve path
67 protective cap
68 protective cap securing device
69 overall housing
70 density monitor housing part
71 connection housing part
72 valve housing region

What is claimed is:

1. A multi-path valve device (44) for connecting a monitoring device (63) for monitoring at least one gas parameter to an electrical system (40) containing a harmful gas and to be monitored with regard to the gas parameter, comprising a first valve path (64), which is designed as a gas connection (13) for connecting the valve device (44) to the system (40), a second valve path (65), which is adapted for gas transfer to the monitoring device (63), a third valve path (66), which is adapted for gas transfer to a testing device (19) for testing at least one function of the monitoring device (63), and an automatic switching device (56) for selectively automatically connecting the second valve path (65) to the first valve path (64) or the third valve path (66).

2. The multi-path valve device (44) according to claim 1, characterized in that the second valve path (65) contains a check valve arrangement (58) which is pre-loaded into a closing position to close the second valve path (65) and which can be moved to the opening position by connection of the monitoring device (63).

3. The multi-path valve device (44) according to claim 2, characterized in that the check valve arrangement (58) has a check valve opener (7) which is pre-loaded into its closed position and, when the monitoring device (63) is connected, is detected by a connecting element of the monitoring device (63) in order to move the opener (7) into its opening position against its pre-load by the connection.

4. The multi-path valve device (44) according to claim 1, characterized in that the switching device (56) comprises a valve tappet (2) pre-loaded into a first switching position in which the third gas connection (15) is closed and the first gas connection (13) is connected to the second valve path (65) and movable to a second switching position in which the first gas connection (13) is closed and the second valve path (65) is connected to the third gas connection (15) by connecting the testing device (19) to the third gas connection (15).

5. The multi-path valve device (44) according to claim 4, characterized in that the valve tappet (2) comprises a projection or pin (3) which, when the testing device (19) is connected, is engaged by a connecting element of the testing device (19) and is urged against its pre-load from the first switching position into the second switching position.

6. The multi-path valve device (44) according to claim 1, characterized in that at least one sensor device (18) for detecting at least one parameter which is selected from the group of parameters comprising temperature, humidity, type of gas and presence of a decomposition product is in fluid communication with the first gas connection (13) and/or the second valve path (65).

7. The multi-path valve device (44) according to claim 1, characterized in that the first valve path (64) is designed as a first gas connection (13) and that
a) the second valve path (65) is designed as a second gas connection (14) for connecting a monitoring system (46) to the multi-path valve device (44) and/or
b) the third valve path (66) is designed as a third gas connection (15) for connecting the testing device (19).

8. A monitoring system (43), comprising the multi-path valve device (44) according to claim 1 and a monitoring device (63) to monitor at least one gas parameter of a harmful gas in an electrical system (40).

9. The monitoring system (43) according to claim 8, characterized in that the monitoring device (63) and the multi-path valve device (44) are separately formed, with the monitoring device (63) being connectable to the second valve path (65),
or that the monitoring device (63) and the multi-path valve device (44) are integrated into a common unit or a common housing.

10. The monitoring system (43) according to claim 8, characterized in that the monitoring device (63) at least comprises a density monitor (20) and/or a sensor device (18).

11. A monitoring arrangement (42), comprising the monitoring system (43) according to claim 8 and a testing device (19) for testing at least one function of the monitoring system (43).

12. The monitoring arrangement (42) according to claim 11, characterized in that the testing device (19) is connected to the third valve path (66) which is designed as a third gas connection (13).

13. An electrical system (40), comprising a gas space (17) filled with a harmful gas and
a) the multi-path valve device (44) according to claim 1 for connecting a monitoring device (63) for monitoring at least one gas parameter to the gas space (17) or
b) the monitoring system (43) according to claim 8 or
c) the monitoring arrangement (42) according to claim 11.

* * * * *